(12) United States Patent
Nielsen et al.

(10) Patent No.: US 8,053,559 B2
(45) Date of Patent: Nov. 8, 2011

(54) BIODEGRADABLE SCAFFOLD WITH ECM MATERIAL

(75) Inventors: Peter Sylvest Nielsen, Vaerloese (DK); Brian Nielsen, Goerloese (DK); Lene Karin Jespersen, Fredensborg (DK); Hanne Everland, Bagsvaerd (DK); Lene Feldskov Nielsen, Copenhagen (DK)

(73) Assignee: Coloplast A/S, Humlebaek (DK)

( * ) Notice: Subject to any disclaimer, the term of this patent is extended or adjusted under 35 U.S.C. 154(b) by 624 days.

(21) Appl. No.: 12/083,624

(22) PCT Filed: Oct. 26, 2006

(86) PCT No.: PCT/EP2006/067837
§ 371 (c)(1),
(2), (4) Date: Apr. 16, 2008

(87) PCT Pub. No.: WO2007/048831
PCT Pub. Date: May 3, 2007

(65) Prior Publication Data
US 2009/0280154 A1    Nov. 12, 2009

Related U.S. Application Data

(60) Provisional application No. 60/733,208, filed on Nov. 4, 2005.

(30) Foreign Application Priority Data

Oct. 27, 2005  (DK) ................................. 2005 01490
Apr. 24, 2006  (DK) ................................. 2006 00570

(51) Int. Cl.
*C07K 14/00*    (2006.01)
(52) U.S. Cl. ..................................................... 530/350
(58) Field of Classification Search .................... 530/350
See application file for complete search history.

(56) References Cited

U.S. PATENT DOCUMENTS

| | | | | |
|---|---|---|---|---|
| 5,709,934 A * | 1/1998 | Bell et al. | ................... | 428/305.5 |
| 5,749,895 A | 5/1998 | Sawyer et al. | | |
| 5,800,537 A * | 9/1998 | Bell | ............................ | 424/93.1 |
| 5,866,165 A * | 2/1999 | Liu et al. | ...................... | 424/486 |
| 5,891,558 A * | 4/1999 | Bell et al. | ...................... | 428/218 |
| 5,948,429 A * | 9/1999 | Bell et al. | ...................... | 424/426 |
| 7,569,233 B2 | 8/2009 | Malaviya et al. | | |
| 2004/0110439 A1 | 6/2004 | Chaikof et al. | | |

FOREIGN PATENT DOCUMENTS

| | | |
|---|---|---|
| EP | 1 481 694 A1 | 12/2004 |
| EP | 1 498 128 A1 | 1/2005 |
| WO | WO 97/18842 | 5/1997 |
| WO | WO 00/16818 | 3/2000 |

OTHER PUBLICATIONS

Badylak, S.F., et al., "The Extracellular Matrix as a Scaffold for Tissue Reconstruction," Semin. Cell Dev. Biol. Oct. 2002, vol. 13, No. 5, pp. 377-383.
Badylak, S.F., et al., "Small Intestinal Submucosa: a substrate for in vitro cell growth," J. Biomater. Sci. Polym. Ed., vol. 9, pp. 863-878, Feb. 1998.
Lindberg, K., et al., "Porcine Small Intestine Submucosa (SIS): a bioscaffold supporting in vitro primary human epidermal cell differentiation and synthesis of basement membrane proteins," Burns, May 2001, vol. 27, No. 3, pp. 254-266.
Hodde, J.P., et al., "Vascular Endothelial Growth Factor in Porcine-Derived Extracellular Matrix," Endothelium, 2001, vol. 8, No. 1, pp. 11-24.
Voytik-Harbin, S.L., et al., "Identification of Extractable Growth Factors from Small Intestinal Submucosa," J. Cell Biochem, 1997, vol. 67, pp. 478-491.
McDevitt, C.A., et al., "Transforming Growth Factor-beta1 in a Sterilized Tissue Derived from the Pig Small Intestine Submucosa," J. Biomed. Mater. Res. Nov. 2003, 1;67A (2): vol. 67A, pp. 637-640.
Gilbert, T.W., "Production and Characterization of ECM Powder: Implications for Tissue Engineering Applications," Biomaterials, vol. 26, No. 12, 2005, pp. 1431-1435.
Pandit, A., et al., "The Effect of TGF-beta Delivered Through a Collagen Scaffold on Wound Healing," J. Invest. Surg., vol. 12, No. 2, 1999, pp. 89-100.
Pandit, A. et al., "Investigation of Cidic Fibroblast Growth Factor Delivered Through a Collagen Scaffold for the Treatment of Full-Thickness Skin Defects in a Rabbit Model," Plast. Reconstr. Surg., vol. 101, No. 3, 1998, pp. 766-775.
Pandit, A., et al., "Fibrin Scaffold as an Effective Vehicle for the Delivery of Acidic Fibroblast Growth Factor (FGF-1)," J. • Biomater. Appl., vol. 14, No. 3, 2000, pp. 229-242.
Obara, K., et al., "Acceleration of Wound Healing in Healing-Impaired db/db mice with a Photocrosslinkable Chitosan Hydrogel Containing Fibroblast Growth Factor-2," Wound. Repair Regen., vol. 13, No. 4, 2005, pp. 390-397.
Yamamoto, M., et al., "Bone Regeneration by Transforming Growth Factor Beta1 Released from a Biodegradable Hydrogel," J. Control Release, vol. 64, No. 1-3, 2000, pp. 133-142.
Miyoshi, M., et al., "Effects of bFGF Incorporated into a Gelatin Sheet on Wound Healing," J. Biomater. Sci. Polym. Ed. vol. 16, No. 7, 2005, pp. 893-907.
Ulubayram, K., et al., "EGF Containing Gelatin-Based Wound Dressings," Biomaterials, vol. 22, No. 11, 2001, pp. 1345-1356.

* cited by examiner

*Primary Examiner* — Karen Carlson
(74) *Attorney, Agent, or Firm* — Jacobson Holman PLLC

(57) ABSTRACT

We add discontinuous regions of Extra Cellular Matrix (ECM) to a biodegradable scaffold. Hereby it is possible to combine the range of physical properties the scaffold can offer with the reconstructive properties of the ECM. The optimal amount of discrete ECM material for each application is disclosed and this concentration is equally distributed in the dressing hence avoiding unnecessary high concentrations of ECM. In addition to the effect of the ECM, the porous structure of the base material provides the cells with a structure for in-growth.

11 Claims, 7 Drawing Sheets

BIODEGRADABLE SCAFFOLD WITH ECM MATERIAL

Figure 1:
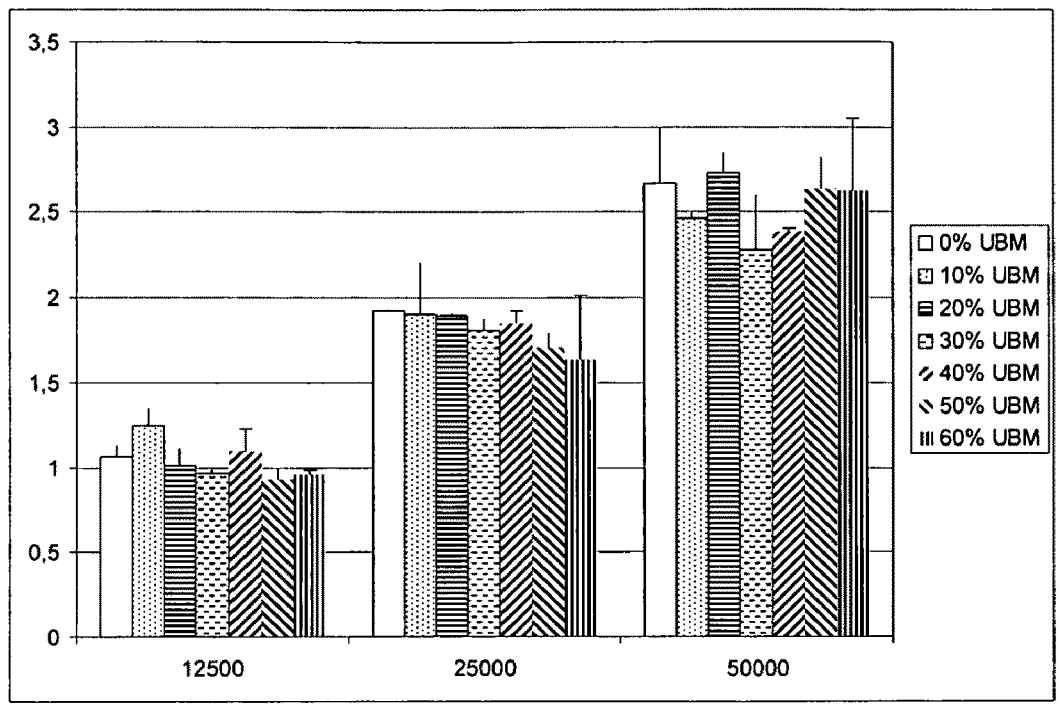

This is a national stage of PCT/EP2006/067837 filed Oct. 26, 2006 and published in English, claiming benefit of U.S. provisional application No. 60/733,208, filed Nov. 4, 2005.

FIELD OF THE INVENTION

The present invention relates to a scaffold comprising a biodegradable layer having ECM material in the form of flakes, fibres, particles, powder or the like incorporated in the biodegradable layer.

BACKGROUND

Scaffolds are structures used to guide the organization, growth and differentiation of cells in the process of forming new functional tissue.

To achieve the goal of tissue reconstruction, scaffolds must meet some specific requirements. A high porosity and an adequate pore size are necessary to facilitate cell growth and diffusion throughout the whole structure of both cells and nutrients. Biodegradability is essential since scaffolds need to be absorbed by the surrounding tissues without the necessity of a surgical removal.

Many different materials (natural and synthetic, biodegradable and permanent) have been investigated for use as scaffolds. Most of these materials have been known in the medical field before the advent of tissue engineering as a research topic, being already employed as bioresorbable sutures. Examples of these materials are collagen or some linear aliphatic polyesters.

However, when testing laboratory made scaffolds in vivo, it is often seen, that the cells do not grow readily into these scaffolds, maybe due to the fact that no biological signal molecules, e.g. growth factors, are found in synthetically made scaffolds.

In order to improve the biological properties of the scaffolds and to accelerate wound healing, several labs have added growth factors to a synthetic scaffold and seen beneficial effects on wound healing. In all of these publications a single growth factor has been incorporated in a sheet or hydrogel. The growth factors examined have been FGF-2 (1; 2), β-FGF-2 tested in a concentration of 25 µg/cm$^2$ (2), FGF-1 (3; 4), EGF (5)(14), or TGF-β (6; 7) in a concentration of 2 µg/cm$^2$. Acellular extracellular matrices (ECM) from warm-blooded vertebras are used extensively in tissue engineering and plastic surgery (8). It has been shown that acellular ECM contains several growth factors (9-11). ECMs contain a lot of biologic molecules and it has been shown that cells readily populate these sheets of concentrated ECM (12; 13). The ECMs on the market today are of human or porcine origin. The cells are removed from the tissue and the tissue is subsequently lyophilized and cut into sheets. The sheets of porcine origin come in different sizes. The price of these sheets is very high. The sheets are fairly stiff when un-hydrated. An example is the sheets from the company Acell. They sell sheets of ECM (Urinary Bladder Matrix, UBM) that accelerate the wound healing. Such sheet (7×5 cm) weighs about 100 mg and has a density of about 190 mg/cm$^3$.

Use of ECMs or ECM proteins in wound care is known. These products are in the form of sheets or hydrogels. Examples of sheet products are OASIS from Healthpoint (lyophilized porcine ECM sheet) and Graftjacket from Wright medical (lyophilized human ECM sheet). The sheets provide both a scaffold as well as a complex mixture of proteins to the cells of the wound. Examples of non-scaffold products containing ECM proteins on the market, is Xelma from Mölnlycke, which is a hydrogel that contains a protein extract from ECM of developing pig teeth.

SUMMARY

The present application discloses that the growth promoting effects of ECM is maintained if the ECM is incorporated into a scaffold. We demonstrate that when using scaffolds containing ECM material, higher concentrations of ECM surprisingly do not give better cell morphology. Concentrations lower than 60% is sufficient to obtain the best cell morphology and distribution. In addition it is shown that by varying the concentration of discrete ECM material in scaffolds the physical characteristic of the scaffold changes but that the changes are depending on the material of the scaffold. The present application takes this knowledge to the patient by showing a sterilisation strategy that maintains the biological activity of the ECM material after sterilisation.

DETAILED DISCLOSURE

The present invention relates to a temporary composite scaffold comprising discrete ECM particles.

By adding discontinuous regions of ECM to a scaffold it is possible to combine the range of physical properties (e.g. strength, softness, flexibility, durability) the scaffold can offer with the reconstructive properties of the ECM. In addition, the price of such scaffold will be lower than other ECM scaffolds both because the powder is a waste-product from the production of acellular ECM sheets and because the optimal amount of discrete ECM material for each application can be determined and equally distributed in the dressing hence avoiding unnecessary high concentrations of ECM. In addition to the effect of the ECM, the porous structure of the base material provides the cells with a structure for in-growth. In one embodiment a discontinuous region of ECM is obtained by adding discrete ECM material, such as particles, flakes, fibres or powder.

A discrete phase of ECM material means material of ECM that is distinguished in their form and density from the ground material that they are embedded in. This can be demonstrated by histology sections as seen in example 5 or by scanning electron microscope (SEM) seen in example 6. By adding discontinuous regions of ECM, we can control the concentration of ECM. As shown in the examples (e.g. examples 2 and 3), it is important that concentration is controlled to optimise cell growth.

It is preferred, that the ECM material is added to the scaffold before scaffold formation (e.g. freeze-drying). In this way, the ECM material is homogeneously distributed in the scaffold. That is, in the time it takes to solidify the scaffold (e.g. during freezing) the density of ECM material might be somewhat higher in one end of the scaffold than the other. However, in the present context a homogeneous distribution allows for such density gradient through the scaffold provided that the density in the centre of the scaffold is >0. Thus, a preferred embodiment relates to a temporary, continuous scaffold comprising homogeneously distributed discontinuous regions of ECM wherein the concentration of discontinuous regions of ECM is between 20% (w/w) and 60% (w/w).

In the present context, a temporary scaffold means a scaffold that disappears; is hydrolysed, is broken down, is biodegraded/bioresorbable/bioabsorbable, is dissolved or in other ways vanish from the wound site. This is a huge clinical advantage as there is nothing to remove from the wound.

Thus, the newly formed tissue is not disturbed or stressed by removal of the temporary scaffold. It is typically preferred that the scaffold is broken down during 1 day to 10 weeks—depending on the application. For open wound applications, it is preferred that the scaffold is broken down during 1-10 days, such as 2-7 days. In one aspect of the invention, the scaffold is biodegradable.

In one embodiment the scaffold is a continuous scaffold. That is a scaffold of a continues phase. A continuous scaffold with discontinuous regions results in a composite material. As with other composite materials, this is an engineered material made from two or more constituent materials with significantly different physical or chemical properties and which remains separate and distinct within the finished structure.

Extracellular matrix (ECM) is the non-cellular portion of animal or human tissues. The ECM is hence the complex material that surrounds cells. Consequently, it is preferred that the discontinuous regions of ECM are cell free regions. Cell free regions are obtained by the use of physical, enzymatic, and/or chemical methods. Layers of cells can be removed physically by e.g. scraping the tissue. Detergents and enzymes may be used to detach the cells from one another in the tissue. Water or other hypotonic solutions may also be used, since hypotonicity will provoke the cells in the tissue to burst and consequently facilitate the decellularization process.

Another way to obtain cell free regions is by adding the ECM powder (discontinuous regions of ECM) to the scaffold matrix. A cell-free product minimizes the risk any immune rejection once implanted, since components of cells may cause an immunogenic response.

In broad terms there are three major components in ECMs: fibrous elements (particularly collagen, elastin, or reticulin), link proteins (e.g. fibronectin, laminin), and space-filling molecules (usually glycosaminoglycans). ECMs are known to attract cells and to promote cellular proliferation by serving as a reservoir of growth factors and cytokines (9; 10). A temporary scaffold containing particulate ECMs used in a wound will be populated by cells both from the wound edges as well as cells from the circulating blood. As the cells invade the scaffold, the scaffold material will be degraded and eventually the scaffold will be replaced with new tissue.

The concentration of the discontinuous regions of ECM is preferably higher than 15% (w/w), that is higher than 20% (w/w), such as higher than 30% (w/w). The concentration of the discontinuous regions of ECM is preferably lower than 95% (w/w), that is lower than 90% (w/w), such as lower than 80% (w/w), or lower than 70% (w/w). In a particular preferred embodiment of the invention the concentration is between 20% (w/w) and 60% (w/w), such as between 20% (w/w) and 40% (w/w).

The skin of humans comprises an upper layer of epidermis, formed by inter alia keratinocytes. Below epidermis is dermis, formed by inter alia fibroblasts, but also endothelial cells.

When promoting growth of fibroblasts, the present examples (e.g. example 3) show that increasing the concentration of ECM from 0% (w/w) to about 60% (w/w) results in a marked improvement in the number of cells on the surface of the scaffold and in the cell morphology. Thus, one aspect of the invention relates to a wound care device comprising 40% (w/w) to 60% (w/w) ECM to promote growth of fibroblasts.

When promoting growth of keratinocytes, the present examples using gelatine scaffolds show that increasing the concentration of ECM from 0% (w/w) to about 25% (w/w) results in a marked improvement in the ability of the cells to grow together (as keratinocytes should do), in the cell morphology and in the total number of cells. However, increasing the concentration of ECM above 40% (w/w) results in a decrease in the promotion of cell growth in terms of number of cells on the surface, their morphology and the number of cells. Thus, one aspect of the invention relates to a wound care device comprising 20% (w/w) to 30% (w/w) ECM to promote growth of keratinocytes.

The wound dressing of the present invention may comprise multiple layers. These layers could include 1 or more layers of biodegradable material, which all optionally comprise ECM. If ECM is incorporated in more than one layer the dose may vary across the layers. In one embodiment, the first layer comprises 40% (w/w) to 60% (w/w) ECM; the second layer 20% (w/w) to 30% (w/w) ECM.

In another embodiment, the scaffold is designed for growth stimulation of different cell-types. That is, for growth stimulation of fibroblasts the optimal concentration is 40% (w/w)-60% (w/w) ECM, the optimal concentration for endothelial cells is 30% (w/w)-60% (w/w), whereas for growth stimulation of keratinocytes, the optimal concentration is 20% (w/w) to 30% (w/w). One embodiment of the invention relates to a wound care device comprising two scaffolds, a first scaffold for stimulation of fibroblasts with a concentration of discontinuous regions of ECM of 40% (w/w)-60% (w/w), and a second scaffold for stimulation of keratinocytes with a concentration of discontinuous regions of ECM of 20% (w/w) to 30% (w/w). A third scaffold can be added to the wound care device with a concentration of discontinuous regions of ECM material of 20% (w/w) to 30% (w/w).

The present data enable use of a scaffold comprising 40% (w/w)-60% (w/w) of discontinuous regions of ECM for stimulation of fibroblast growth. The present data also enable use of a scaffold comprising 20% (w/w) to 30% (w/w) of discontinuous regions of ECM for stimulation of keratinocyte growth.

It is our experience, that when promoting growth of fibroblasts, the growing fibroblasts will excrete growth factors inducing growth of keratinocytes. Thus, a preferred aspect of the invention relates to a scaffold wherein the concentration of discontinuous regions of ECM is between 40% (w/w) and 50% (w/w). Hereby, fibroblast growth is promoted such that keratinocyte growth is subsequently promoted and the wound is healed.

The concentration of ECM in the scaffold structure is calculated as weight/weight percent. That is: concentration (w/w)=$M_{ECM}/(M_{ECM}+M_{scaffold})\times 100\%$, where $M_{ECM}$ is the mass in gram of ECM and $M_{scaffold}$ is the mass in gram of scaffold (not containing ECM).

In a dissolvable scaffold (e.g. MPEG-PLGA) you dissolve the scaffold in solvent and filter the ECMs. After freezedrying, the material is weighted.

In a non-dissolvable scaffold the material is embedded in an appropriate embedding material (e.g. paraffin), sectioned in a statically representative number and stained using a appropriate stain which only stains the ECMs and not the scaffold materials. Using image analysis the amount of ECMs are calculated in relation to scaffold.

Preferred ECM materials contain bioactive ECM components derived from the tissue source of the materials. For example, they may contain Fibroblast Growth Factor-2 (basic FGF), Transforming Growth Factor-beta (TGF-beta) and vascular endothelial growth factor (VEGF). It is also preferred that ECM base materials of the invention contain additional bioactive components including, for example, one or more of collagens, glycosaminoglycans, glycoproteins and/or proteoglycans. The ECM may include the basement membrane, which is made up of mostly type IV collagen, laminins and proteoglycans. The ECM material of the invention is preferably prepared from tissue harvested from animals raised for meat production, including but not limited to, pigs, cattle and sheep. Other warm-blooded vertebrates are also useful as a source of tissue, but the greater availability of such tissues from animals used for meat production makes such tissue preferable. Pigs that are genetically engineered to be free of the galacatosyl, alpha 1,3 galactose (GAL epitope) may be used as the source of tissues for production of the ECM material. In a preferred embodiment the ECM will be of porcine origin.

The ECM material can be obtained from any animal. It could be derived from, but not limited to, intestinal tissue, bladders, liver, spleen, stomach, lymph nodes or skin. ECM derived from human cadaver skin, porcine urinary bladder submucosa (UBS), porcine urinary bladder matrix (UBM), or porcine small intestinal submucosa (SIS) are particularly preferred.

Human tissue is preferably avoided to minimize transfer of diseases. Thus, in a preferred embodiment the discontinuous regions of ECM are obtained from animal tissues. Due to species similarity, it is preferred to use ECM from warm-blooded mammal.

In a particular preferred embodiment the discontinuous regions of ECM are UBM (Urinary Bladder Matrix) particles. The UBM material comprise a unique cocktail of ECM proteins of which a few have been quantified: TGF-$\beta$ 293±8 pg/g, b-FGF 3862±170 pg/g, and VEGF 475±22 pg/g (that is pg VEGF/g UBM). With an average density of 3 mg/cm$^2$, the concentration is about TGF-$\beta$: 0.9 pg/cm$^2$ in an ECM sheet, b-FGF: 11.6 pg/cm$^2$ and VEGF 1.4 pg/cm$^2$.

One aspect of the invention is to provide a scaffold with constant dosing of growth factors. One property of the scaffold used in the present invention is to distribute the discontinuous regions of ECM within the porous base material, such that the ECM is accessible for the cells. When the cells migrate through the scaffold matrix, the discontinuous regions of ECM are exposed to protease activity and degraded which are believed to result in release of the biologically active components from the discontinuous regions of ECM (14). Thus, the release of biologically active components can be kept somewhat constant throughout the period of use, thereby providing a somewhat constant dosing to the wound bed and cells. In one embodiment, the discontinuous regions of ECM are equally distributed within the temporary scaffold.

ECM comes in several micronized forms: e.g. as particles, flakes, fibres or powder. All of these are considered discontinuous regions of ECM, i.e. discrete ECM materials.

A preferred form of discontinuous regions of ECM is ECM particles. Preferably particles with a mean diameter of approximately 150 μm. This is determined by a Mastersizer 200 from Malvern Instrument for volume weighted mean. For example, a surface weighted mean of 100 μm, can have the smallest particles of 3 μm, the largest particles of 750 μm. A volume weighted mean would, in this case be 250 μm.

By distributing the discontinuous regions of ECM in a porous scaffold, it is possible to optimise the physical properties (e.g. strength, softness, flexibility, durability) of the scaffold without major impact from the discontinuous regions of ECM.

In order to obtain both the beneficial effect of the ECMs, and the physical properties a porous scaffold can offer, particulate ECM can be included in a wound dressing such as a scaffold and be used for tissue engineering (e.g. remodelling of soft tissue engineering, bone, cartilage, ligaments and tendons) or dental applications. This porous scaffold should preferably be of a material that is biodegradable. The temporary scaffold may be either in a lyophilised form, in a fibrous form (woven or non-woven), in a foamed form or as a film. In all forms the discontinuous regions of ECM are accessible to the cells on both the outer and inner surface of porous/fibrous structure.

The material used for the scaffold may be any biodegradable material, from both synthetic and of natural sources. Of the scaffolds constructed from natural materials, particular preferred are those based on derivatives of the extracellular matrix. Examples of such materials are protein materials, such as collagen or fibrin, and polysaccharidic materials, like chitosan or glycosaminoglycans (GAGs).

In one embodiment the biodegradable scaffold is made of protein containing substances. This will enable degradation by proteolytic enzymes. Such scaffolds are preferably made of proteins such as collagen, keratin, fibrin, elastin, laminin, vimentin, vitronectin, fibronectin, fibrinogen and derivatives of these and the like or denaturated proteins such as gelatin.

By making scaffolds using polymer materials such as gelatin, fibrin, hyalouronic acid, collagen, chitin, chitosan, keratin, alginate, PLA and PLGA it is possible to vary the scaffolds physical characteristics (strengths, softness, flexibility) through combinations and modifications.

In another embodiment the biodegradable scaffold is made of carbohydrate/polysaccharide containing substances. This will enable degradation by hydrolysis and enzymatic degradation of the polysaccharides. Such scaffolds are preferably made of polysaccharides such as heparan sulfate, chondroitin sulfate, dermatan sulfate, heparin, keratan sulfate and derivatives of these, alginates, HSC cellulose and cellulose derivatives (CMC), some alginates, chitosan, chitin, pectin and pectin derivatives, hyaluronic acid and proteoglycans (mucopolysaccharides) and derivatives of these.

In another aspect the temporary scaffold is synthetic. Such scaffolds are mainly degraded by hydrolysis in combination with enzymatic digestion. These scaffolds are preferably made from materials selected from the group consisting of PLA (polylactide), PGA (polyglycolide), PLGA (poly(lactide-co-glycolide)), MPEG-PLGA, PCL (polycaprolactone), poly ortho esters, polydioxanone, polyanhydrides, polyhydroxyalkanoate, and co-polymers of the above-mentioned materials.

Examples of well known natural scaffolds/gels are collagen based (3; 6), fibrin based (4), chitosan based (1), or gelatine based (2; 7).

A commonly used synthetic material is PLA—polylactic acid. This is a polyester, which degrades within the human body to form lactic acid, a naturally occurring chemical that is easily removed from the body. Similar materials are polyglycolic acid (PGA) and polycaprolactone (PCL): their degradation mechanism is similar to that of PLA, but they exhibit respectively a faster and a slower rate of degradation compared to PLA. Such MPEG-PLGA polymer can be synthesized as follows: MPEG, DL-lactide, glycolide and 4% (w/v) stannous octanoate in toluene are added to a vial in a glove box with nitrogen atmosphere. The vial is closed, heated and shaken until the contents are clear and homogeneous and then placed in an oven at 120-200° CC for 1 min-24 h. The synthesis can also be made in a solution in a suitable solvent (e.g. dioxane) to facilitate the subsequent purification. Then MPEG, DL-lactide, glycolide, 4% Stannous 2-ethylhexanoate and dioxane are added to a vial in a glove box with nitrogen atmosphere, and treated as above.

The polymer can be purified as follows: The polymer is dissolved in a suitable solvent (e.g. dioxane, tetrahydrofuran, chloroform, acetone), and precipitated with stirring in a non-solvent (e.g. water, methanol, ethanol, 1-propanol or 2-propanol) at a temperature of −40° C.-40° C. The polymer is left to settle, solvent discarded and the polymer is dried in a vacuum oven at 40° C.-120° C./overnight.

As illustrated in the foregoing, the base material of the scaffold can be made of material of synthetic and/or natural origin—including combinations thereof. Hence the scaffold can comprise combinations of proteins, polysaccharides and synthetic polymers.

One function of the scaffold used in the present invention is to provide a matrix promoting cell growth. One criterion to promote cell in-growth into the scaffold is a scaffold that is solid at room temperature. That is, the scaffold has a fixed physical structure, a bi-continuous structure. By this structure, cells are helped to migrate through the scaffold and form new tissue.

Another criterion to promote cell growth is a scaffold that has open pores, or at least a porosity that allows cell migration.

Porosity is defined as $P=1-\rho$ (V/M)
where P is the scaffold porosity, $\rho$ the density of the polymeric system used, M the weight, and V the volume of the fabricated scaffolds.

One embodiment of the invention relates to a porous scaffold comprising discontinuous regions of ECM as described herein. As illustrated in the examples, a porosity of more than 50% enables cell growth. Thus, an a preferred embodiment the scaffold as described comprises a porosity of more than 50%, such as >80%, even more than 90%, or as porous at 95%.

It is preferred that the porous scaffold has open interconnected pores.

In a preferred embodiment of the invention, the temporary scaffold has a thickness between 0.1 to 8 mm, preferably 0.3 to 3 mm, and even more preferred 0.5 to 2 mm. In a particular preferred embodiment of the invention the thickness of the biodegradable layer is approximately 1 mm. In a preferred embodiment of the invention the biodegradable layer is in direct contact with the wound.

The scaffold according to the present invention is aimed for use as a wound dressing. One factor to bear in mind in wound dressings is to make it soft and conformable. By soft and conformable, in this context, is meant that it is not unpleasant or painful, when applied in an open wound, as the edges will not cut through and stress the sensitive wound surroundings, and the dressing will bend with the curvatures of the wound. This also secures direct contact between the wound area and the ECM containing scaffold.

One example of such soft and conformable matrix is a chitosan, prepared in a 1-2% (w/w) solution and freeze-dried. The result is an open matrix that is soft, that is a scaffold with open interconnected pores. This matrix is also sufficiently open-pored to allow cell growth and migration.

In one set of embodiments, the dressing according to the invention is used for acute wounds, burn wounds, chronic wounds, and/or surgical wounds.

In another embodiment, the dressing according to the invention is used in plastic surgery.

In a related embodiment, the scaffold comprising discontinuous regions of ECM is used for tissue engineering (e.g. remodeling of soft tissue, bone, cartilage, ligaments and tendons) or dental applications.

In many of these uses, it is a requirement that the dressing according to the invention is sterilized. One embodiment of the invention relates to a sterilised, temporary, continuous scaffold comprising discontinuous regions of ECM. This is typically expressed as a temporary, continuous scaffold comprising discontinuous regions of ECM packaged bacterial tight, with a marking on the packaged that this product is sterilized. As illustrated in Example 4, sterilisation by e.g. radiation maintains the biological effect of ECM—dependent on scaffold type. Bacterial tight materials are well known to the skilled person.

REFERENCES

1. Obara, K., Ishihara, M., Fujita, M., Kanatani, Y., Hattori, H., Matsui, T., Takase, B., Ozeki, Y., Nakamura, S., Ishizuka, T., Tominaga, S., Hiroi, S., Kawai, T., & Maehara, T. 2005, "Acceleration of wound healing in healing-impaired db/db mice with a photocrosslinkable chitosan hydrogel containing fibroblast growth factor-2", *Wound. Repair Regen.*, vol. 13, no. 4, pp. 390-397.
2. Miyoshi, M., Kawazoe, T., Igawa, H. H., Tabata, Y., Ikada, Y., & Suzuki, S. 2005, "Effects of bFGF incorporated into a gelatin sheet on wound healing", *J. Biomater. Sci. Polym. Ed*, vol. 16, no. 7, pp. 893-907.
3. Pandit, A., Ashar, R., Feldman, D., & Thompson, A. 1998, "Investigation of acidic fibroblast growth factor delivered through a collagen scaffold for the treatment of full-thickness skin defects in a rabbit model", *Plast. Reconstr. Surg.*, vol. 101, no. 3, pp. 766-775.
4. Pandit, A. S., Wilson, D. J., & Feldman, D. S. 2000, "Fibrin scaffold as an effective vehicle for the delivery of acidic fibroblast growth factor (FGF-1)", *J. Biomater. Appl.*, vol. 14, no. 3, pp. 229-242.
5. Ulubayram, K., Nur, C. A., Korkusuz, P., Ertan, C., & Hasirci, N. 2001, "EGF containing gelatin-based wound dressings", *Biomaterials*, vol. 22, no. 11, pp. 1345-1356.
6. Pandit, A., Ashar, R., & Feldman, D. 1999, "The effect of TGF-beta delivered through a collagen scaffold on wound healing", *J. Invest Surg.*, vol. 12, no. 2, pp. 89-100.
7. Yamamoto, M., Tabata, Y., Hong, L., Miyamoto, S., Hashimoto, N., & Ikada, Y. 2000, "Bone regeneration by transforming growth factor beta1 released from a biodegradable hydrogel", *J. Control Release*, vol. 64, no. 1-3, pp. 133-142.
8. Badylak, S. F. 2002, "The extracellular matrix as a scaffold for tissue reconstruction", *Semin. Cell Dev. Biol.* 2002 October; 13(5): 377-83., vol. 13, pp. 377-383.
9. Hodde, J. P., Record, R. D., Liang, H. A., & Badylak, S. F. 2001, "Vascular endothelial growth factor in porcine-derived extracellular matrix", *Endothelium* 2001; 8 (1):11-24., vol. 8, pp. 11-24.
10. Voytik-Harbin, S. L., Brightman, A. O., Kraine, M. R., Waisner, B., & Badylak, S. F. 1997, "Identification of extractable growth factors from small intestinal submucosa", *J. Cell Biochem.*, vol. 67, pp. 478-491.
11. McDevitt, C. A., Wildey, G. M., & Cutrone, R. M. 2003, "Transforming growth factor—beta1 in a sterilized tissue derived from the pig small intestine submucosa", *J. Biomed. Mater. Res.* 2003 Nov. 1; 67A (2):637-40., vol. 67A, pp. 637-640.
12. Badylak, S. F., Record, R., Lindberg, K., Hodde, J., & Park, K. 1998, "Small intestinal submucosa: a substrate for in vitro cell growth", *J. Biomater. Sci. Polym. Ed*, vol. 9, pp. 863-878.
13. Lindberg, K. & Badylak, S. F. 2001, "Porcine small intestinal submucosa (SIS): a bioscaffold supporting in vitro primary human epidermal cell differentiation and synthesis of basement membrane proteins", *Burns* 2001 May; 27 (3):254-66., vol. 27, pp. 254-266.
14. Li, F., Li, W., Johnson, S., Ingram, D., Yoder, M., & Badylak, S. 2004, "Low-molecular-weight peptides derived from extracellular matrix as chemoattractants for primary endothelial cells", *Endothelium* 2004 May-August; 11(3-4):199.-206., vol. 11, pp. 199-206.

FIGURES

FIG. 1: LDH measurements of scaffolds of gelatine seeded with human primary fibroblasts in three different concentrations (Cell/cm$^2$). The bars represent the growth at day 3, measured as Abs.

Figure 2:
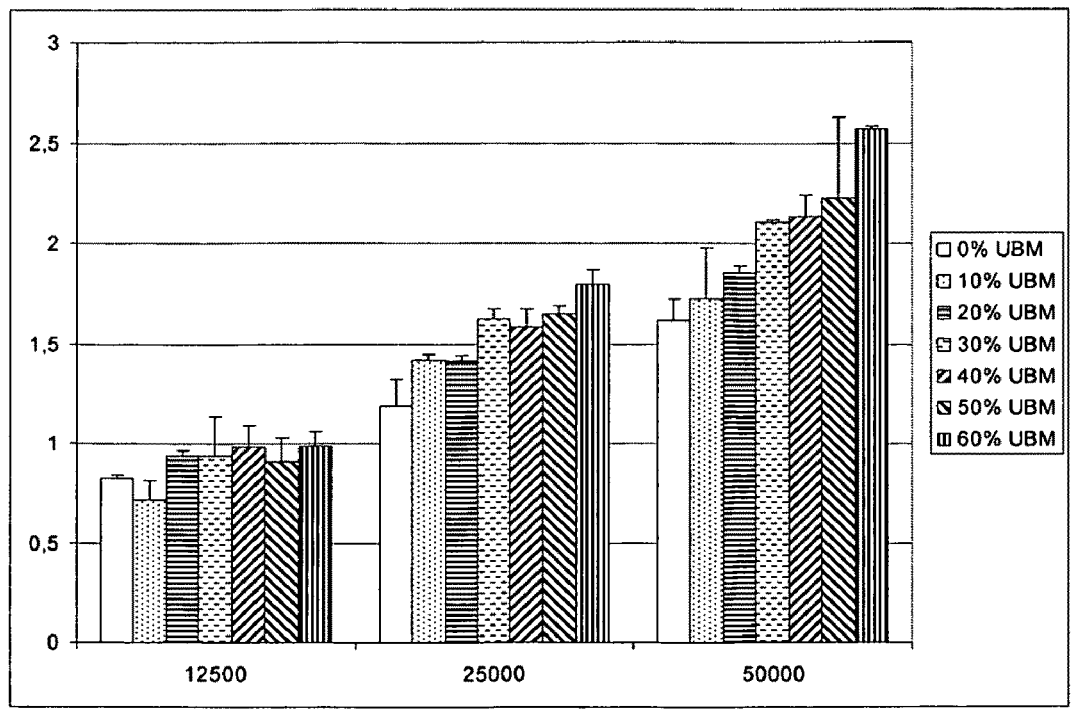

FIG. 2: LDH measurements of scaffolds of MPEG-PLGA seeded with human primary fibroblasts in three different concentrations (Cell/cm$^2$). The bars represent the growth at day 3, measured as Abs.

Figure 3:
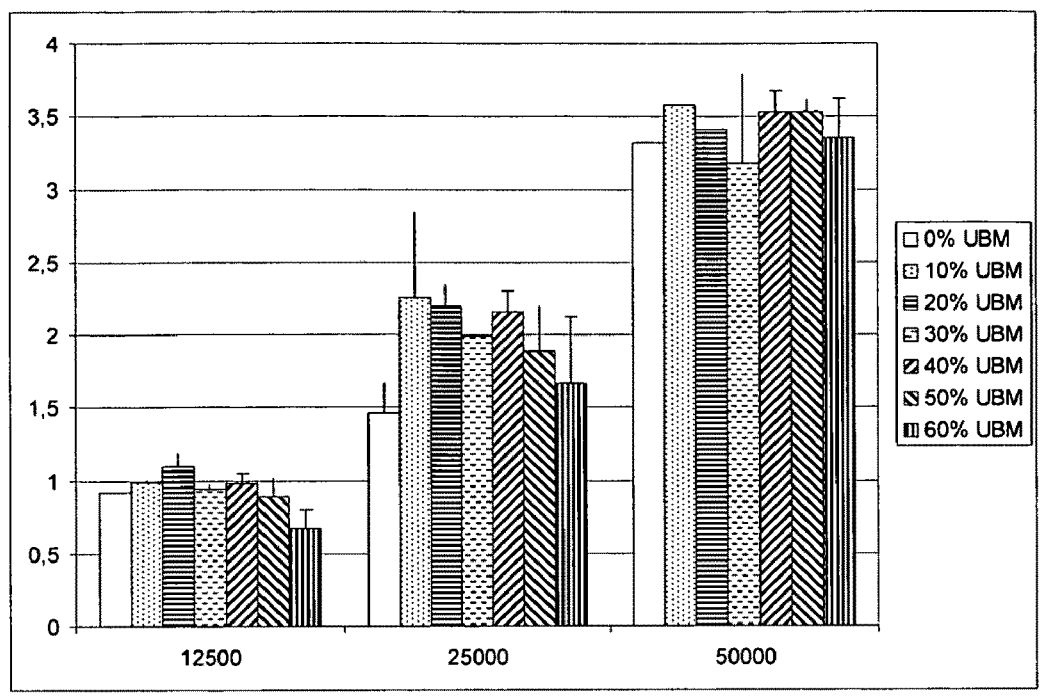

FIG. 3: LDH measurements of scaffolds of gelatine seeded with human primary keratinocytes in three different concentrations (Cell/cm$^2$). The bars represent the growth at day 3, measured as Abs.

Figure 4:
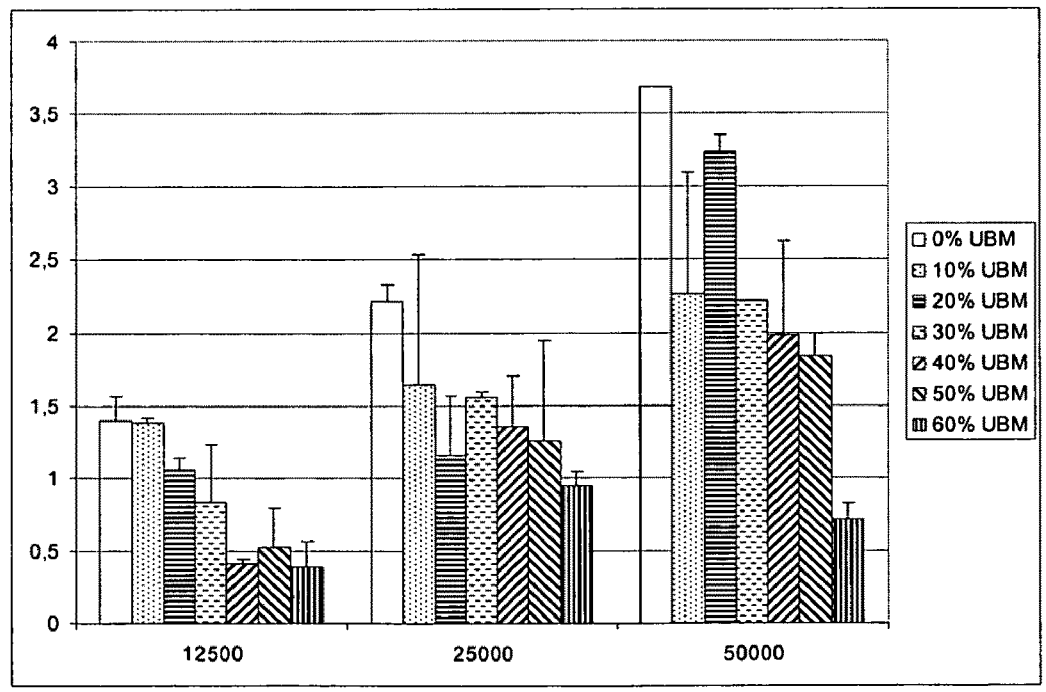

FIG. 4: LDH measurements of scaffolds of MPEG-PLGA seeded with human primary keratinocytes in three different concentrations (Cell/cm$^2$). The bars represent the growth at day 3, measured as Abs.

Figure 5:
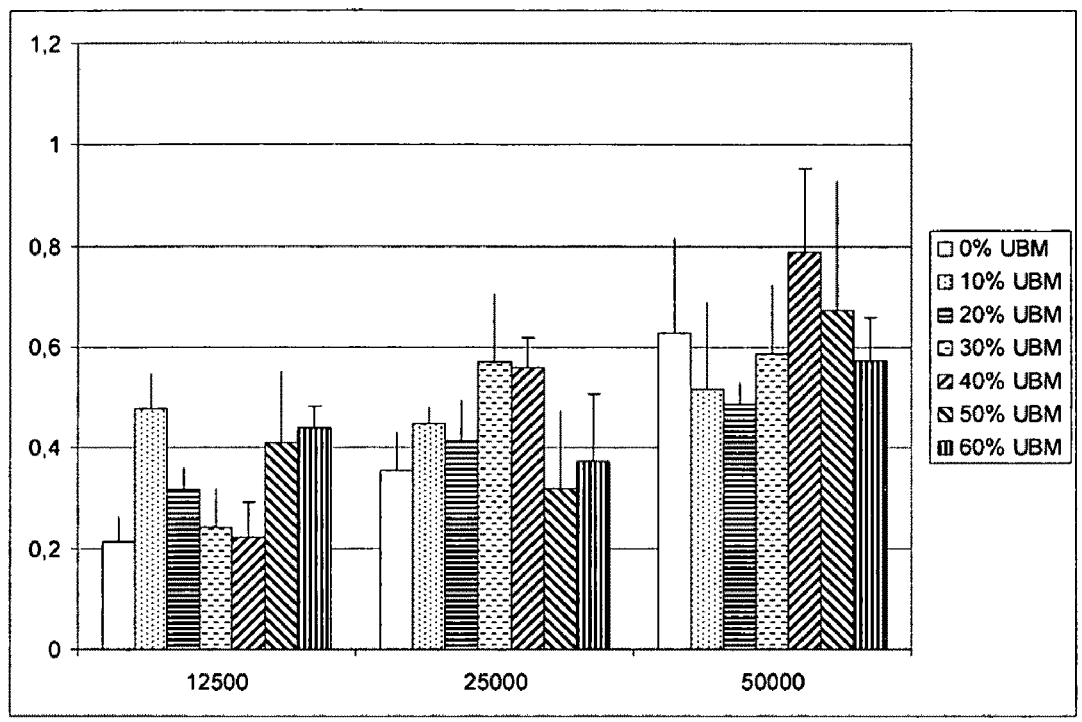

FIG. 5: LDH measurements of scaffolds of gelatine seeded with human umbilical vein endothelial cells in three different concentrations (Cell/cm$^2$). The bars represent the growth at day 3, measured as Abs.

Figure 6:
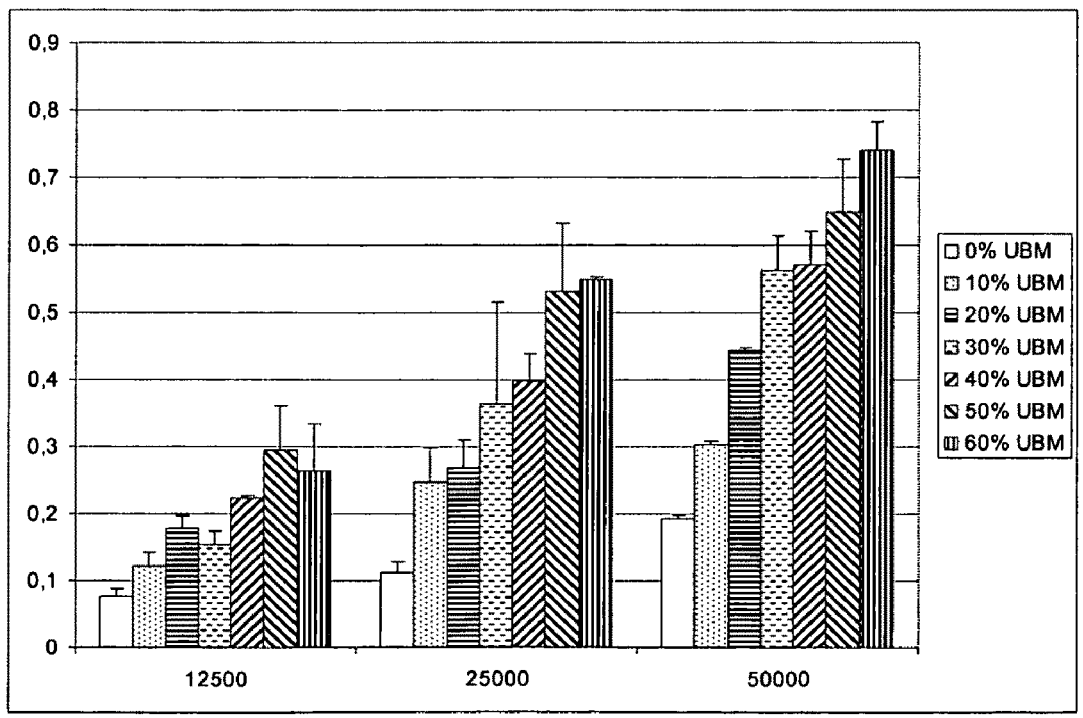

FIG. 6: LDH measurements of scaffolds of MPEG-PLGA seeded with human umbilical vein endothelial cells in three different concentrations (Cell/cm$^2$). The bars represent the growth at day 3, measured as Abs.

Figure 7:
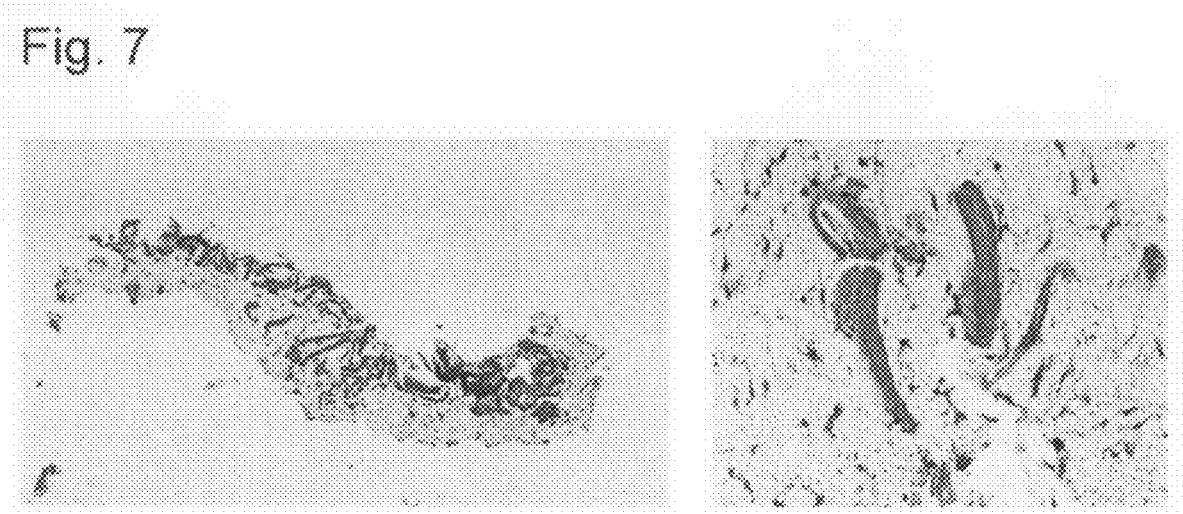

FIG. 7: Digital images of the distribution of ECM particles in the MPEG-PLGA scaffold.

Figure 8:
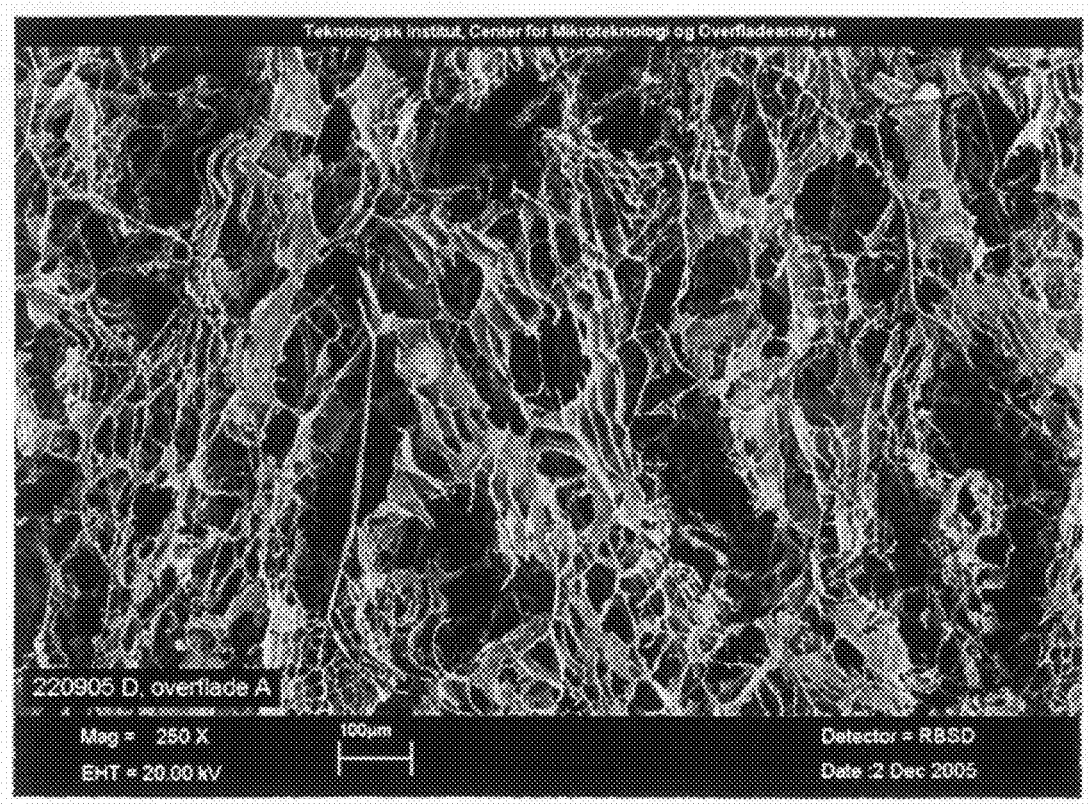

FIG. 8: SEM picture of MPEG-PLGA scaffold (Magnification 250×).

Figure 9:
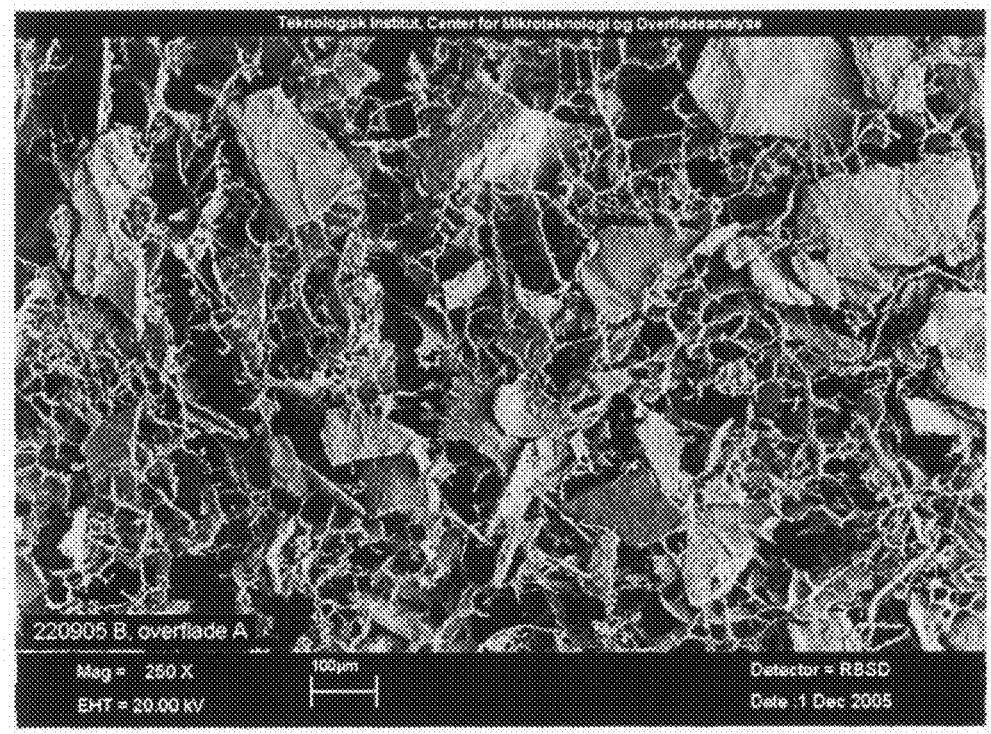

FIG. 9: SEM picture of MPEG-PLGA containing 40% ECM particles (Magnification 250×).

Figure 10:
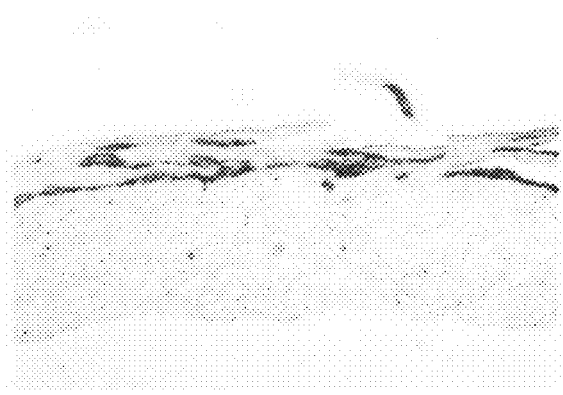

FIG. 10: Digital image of endothelial growth in MPEG-PLGA scaffold.

Figure 11:
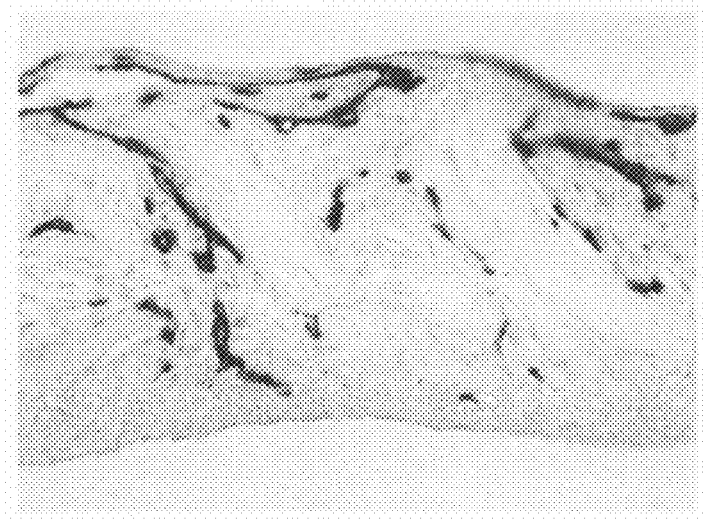

FIG. 11: Digital image of endothelial growth in MPEG-PLGA containing 23% ECM particles.

Figure 12:
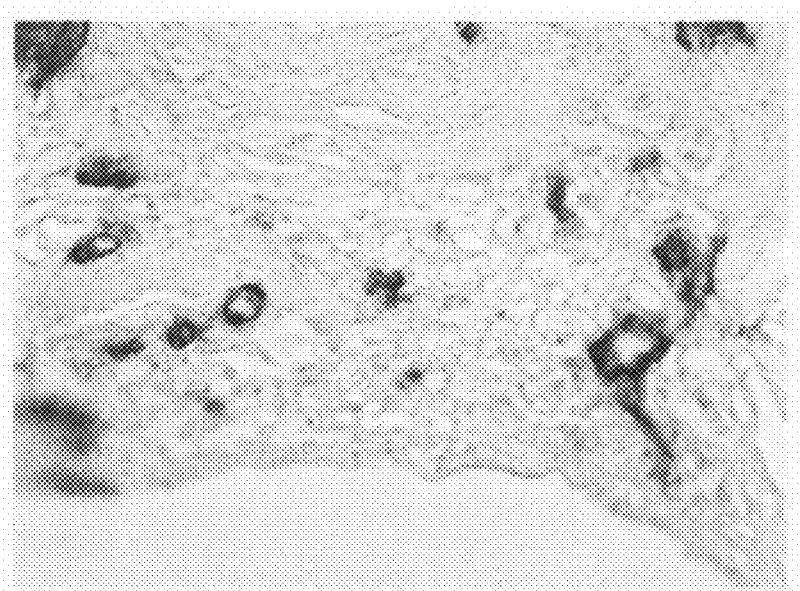

FIG. 12: Digital image of endothelial growth in MPEG-PLGA containing 23% ECM particles showing a magnification of capillary-like morphology in the deeper layers of the scaffold.

EXAMPLES

Example 1

In-Growth of Primary Human Fibroblasts in Synthetic Scaffolds with and without ECM Particles Scaffolds made of biodegradable polyesters containing UBM (Acell) particles (mean diameter of approximately 150 μm) at 40% (w/w) were compared with scaffolds without the ECM particles in a test of cell morphology and 3D growth.

Metoxy-polyethylene glycol—Poly(lactide-co-glycolide) (Mn 2.000-30.000, L:G 1:1) was dissolved in 1,4-dioxane to a 1.5% solution. For the UBM containing scaffold, 0.03 g UBM was added to 3 ml polymer solution (40% w/w drymatter), high-speed-mixed and poured in 3×3 cm mould. The solution was frozen at −5° C. and lyophilized at −20° C. for 5 h and 20° C. for approx 60 h. The samples were subsequently placed in draw (hydraulic pump) in a desiccator for 5 h.

The test of growth and morphology of seeded primary fibroblasts on the surface of the two scaffolds were evaluated. Results from day 1, 3 and 7 were graded from 1-5, with 1 corresponding to worst case and 5 being the best. In the scaffold mixed with ECM particles the distribution and growth of cells was given a grade 5 at all days and were better than the control scaffold (graded 2½ at all days).

Conclusion: The biological activity of the powdered ECM matrix retains activity after incorporation in a synthetic scaffold, and causes a considerably better growth on the scaffold when compared to scaffold alone.

Example 2

Cell Morphology and 3D Growth in Gelatine-ECM Composites Containing 5 Different Concentrations of ECM A study of cell morphology and 3D growth of primary fibroblasts seeded on the surface of gelatine-ECM scaffolds. The gelatine scaffolds were cross-linked by heating and contained increasing concentrations of UBM (0, 12% (w/w), 26% (w/w), 41% (w/w), 51% (w/w) and 58% (w/w)). The concentrations were calculated as amount UBM in relation to total amount of solids meaning a 58% (w/w) scaffold contained 0.05 g polymer and 0.07 g UBM corresponding to 13.8 mg UBM/cm$^3$.

Gelatin from porcine skin, type A, bloom 175 (Sigma) was dissolved in milli-Q water and t-BuOH (95:5) to a 1% solution. For UBM containing samples, the UBM was added to the solution while stirring (0, 12, 26, 41, 51, 58% w/w: 0, 0.007, 0.018, 0.035, 0.053, 0.07 g/scaffold). 5 ml of the UBM containing gelatin solution was poured into the mould (D=5 cm). The mould with the solution was placed in +5° C. for 1 h, then frozen at −20° C. and lyophilized at −20° C. for 5 h and at 20° C. for 36 h. The samples were subsequently cross-linked in vacuum oven at 120° C. for 15 h.

This study showed that by increasing the concentration of UBM in the composite scaffold the fibroblasts were better distributed and had a higher proliferation rate compared to without UBM. In the first couple of days of the study, it was seen that on scaffolds without UBM, cells were only growing in the area where they were applied, while cells were better and more evenly distributed on the surface of scaffolds where the concentration of the UBM were above 26% (w/w). From day 14 it was clear that a lower number of cells were found at the gelatine scaffold without UBM in comparison with composite scaffolds containing UBM. With respect to the cell morphology the fibroblasts had a rounded but adherent morphology at the plain gelatine scaffolds but with increasing amount of UBM an increasing fibroblastic morphology were observed. From 41% (w/w) UBM the best morphology and distribution of the fibroblasts were observed. Increasing the concentration of UBM above 41% (w/w) did not result in better morphology or distribution of the cells in the composite scaffolds.

Example 3

Preparation and Cell Morphology and 3D Growth in Composite Scaffolds of MPEG-PLGA or Gelatine Holding 6 Different Concentrations of ECM Particles Preparation of composite scaffolds of gelatine and ECM: Gelatin from porcine skin, type A, Gelita pharmagrade 832 was dissolved in milli-Q water and t-BuOH (95:5) to a 1% solution. For UBM containing samples, the UBM was added to the solution while stirring; 0, 0.006, 0.013, 0.021, 0.033, 0.05, 0.075 g/scaffold (0, 10, 20, 30, 40, 50, 60% w/w). 5 ml of the UBM containing gelatin solution was poured into the mould (D=5 cm). The mould with the solution was placed in +5° C. for 1 h, then frozen at −20° C. and lyophilized at −20° C. for 5 h and at 20° C. for 18 h. The samples were subsequently cross-linked in vacuum oven at 130° C. for 15 h.

Preparation of composite scaffolds of MPEG-PLGA and ECM: Metoxy-polyethylene glycol-Poly(lactide-co-glycolide) (Mn 2.000-30.000, L:G 1:1) was dissolved in 1,4-dioxane to a 1.5% solution. For UBM containing samples, the UBM was added to the solution while stirring; 0, 0.017, 0.038, 0.064, 0.1, 0.15, 0.225 g/scaffold (0, 10, 20, 30, 40, 50, 60% w/w), high-speed-mixed and 10 ml poured in 7.3×7.3 cm mould. The solution was frozen at −5° C. and lyophilized at −20° C. for 5 h and 20° C. for approx 15 h. The samples were subsequently placed in draw (hydraulic pump) in a desiccator for 24 h.

In order to evaluate the cell morphology and 3D growth of the composite scaffolds, biopsies were punched out of each type of the scaffolds and seeded with primary human fibroblasts (passage 3), human umbilical vein endothelial cells (HUVEC, passage 4), or primary keratinocytes (passage 5) on the surface of the scaffolds with a density of $2.5 \times 10^4$ cells/$cm^2$ in a small volume of growth medium (primary fibroblasts in 10% FCS in DMEM; HUVEC's in EGM-2; primary keratinocytes in KGM-2) containing antibiotics (penicillin, streptomycin and Amphotericin B). The scaffolds were incubated at 37° C. at 5% $CO_2$ before additional growth medium was added. Evaluation of the cells attachment, morphology, growth and population of the scaffold were preformed on day 1, 3 and 7 by staining the cells with neutral red followed by evaluation using an Leica DMIRE2 inverted microscope fitted with a Evolution MP cooled colour camera (Media Cybernetics). Digital images were taken using Image Pro Plus 5.1 software (Media Cybernetics). The number of cells was calculated by using Cytotoxicity Detection Kit (LDH, Roche Diagnostics GmbH). Cells were seeded in three different concentrations ($1.25 \times 10^4$, $2.5 \times 10^4$ and $5 \times 10^4$ cells/$cm^2$) on top of the different scaffold types in the same way as above. The scaffolds were evaluated on day 1, 3 and 7 by washing the scaffolds with PBS before cell lysis using 0.5% CHAPS for 20 h at 4° C. on a flat shaker. Supernatant were transferred to a micro-plate and the amount of LDH measured according to manufactures instructions.

Fibroblasts

The quantitative measurement of fibroblasts showed increasing number of cells with increasing time but no effect was seen between the different concentrations of UBM in the gelatine scaffolds (FIG. 1).

In the MPEG-PLGA scaffolds cells were both increasing with time and amount of UBM in the scaffold (FIG. 2). The cell morphology and 3D growth in the gelatine scaffold without UBM showed in the first days of the study adherent cells growing with a rounded morphology and staying where they were applied. These cells became a little more spindle-shaped during the rest of the study. Adding 10% (w/w) UBM to the scaffold did not change this pattern but at 20% (w/w) UBM an increasing number of cells were becoming spindle-shaped cells with normal fibroblastic morphology and the cells beginning to spread more on the surface. At 30-40% (w/w) a maximum in the ratio of spindle-shaped cells were observed and a change from cells growing on the surface of the scaffolds to a growth where cells were growing in depth of the scaffolds with a more 3D morphology of the cells were seen. In the MPEG-PLGA the same pattern were observed with a few exceptions: Increasing the concentration of UBM gives an increasing number of cells on and in the scaffolds. At 20-30% (w/w) UBM an increasing spreading of cells are seen and more cells with spindle shaped morphology. From 40% (w/w) and above the cells are beginning to grow with 3D morphology and were instead of growing on the surface now growing into the depth of the scaffold.

Keratinocytes

Seeding primary keratinocytes on top of gelatine scaffold with 10% (w/w) UBM showed an increase in the number of cells compared to the scaffold without UBM. A maximum in the number of cells were seen at 10-20% (w/w) UBM in the first days of the study but later in the study 20-30% (w/w) UBM showed maximum effect. Increasing the concentration of UBM resulted in decreasing number of cells on the scaffold (FIG. 3).

On the MPEG-PLGA scaffold the largest number of cells were seen on the scaffold without UBM. Addition of UBM resulted in a decrease in the number of cells found in the scaffold with increasing number of UBM. This effect became more marked at the end of the study. Generally a relative large variation was seen between duplicates due to overlap in concentrations (FIG. 4). The cell morphology and 3D growth showed fine single growing keratinocytes adhering to the surface of the gelatine scaffold. In the 10% (w/w) UBM scaffold an increased number of cells were growing in close connection with each other, like in small sheets. This effect seemed to be more pronounced with time. Increasing the concentration to 20-30% (w/w) UBM were still giving rise to the coherent growing but not as close as in 10% (w/w) UBM. Above 20-30% (w/w) UBM a more single cell growth with increased spreading of the cells were seen together with a decreasing number of cells. In the MPEG-PLGA scaffolds without UBM cells were collected at the centre of the scaffold growing close together almost like in a sheet. Increasing the concentration of UBM resulted in an increasing spreading of the cells together with a decreasing number of cells. In the two highest concentrations dead cells were found trapped into the scaffold structure.

Endothelial Cells

Gelatine scaffolds seeded with Huvec's showed a tendency to increase in number to an optimum around 20-30% (w/w) UBM where after a decrease was seen (FIG. 5). MPEG-PLGA with Huvec's showed that increasing concentrations of UBM resulted in increasing number of cells. Generally large variations were seen with overlaps in adjacent concentrations at both types of scaffolds using Huvec's (FIG. 6). The cell morphology and 3D growth showed that increasing the UBM to 30% (w/w) UBM in the gelatine scaffold gives an increasing ability of the Huvec's to adhere to the surface growing with a flattening morphology with normal short extensions. From 40% (w/w) and up the cells were growing with a more rounded morphology and a decreasing number of cells. In the MPEG-PLGA scaffold without UBM the Huvec's were low in number and growing with rounded morphology resulting in no cells at day 7. Adding 10-20% (w/w) UBM to the scaffold gives a spreading effect of the cells but no effect on the morphology. Increasing the concentration above 30-40% (w/w) gives the optimum cell morphology and increasing the concentration further gives even more 3D growth of the cells. Generally variations were also seen in the cell morphology and 3D growth of both the gelatine and MPEG-PLGA scaffolds containing UBM. Summary of the effect of increasing UBM concentrations on primary fibroblasts, primary keratinocytes and human endothelial cells:

|  | Fibroblasts | | Keratinocytes | | Endothelial | |
|---|---|---|---|---|---|---|
|  | Gelatine | MPEG-PLGA | Gelatine | MPEG-PLGA | Gelatine | MPEG-PLGA |
| cell morphology and 3D growth | 0% = 10% 20% beginning spindle-shaped cells Max 30-40% | 20-60% spreading and spindle-shaped cells 40-60% gives 3D-growth | 10% max sheet-like growth of cells 20-30% sheet-like 40-60% single cells | 0% max sheet-like growth of cells 10-60% decreasing number of cells and sheet-like formation | Increasing 0-30% Max 30% 40-60% decreasing | 0% decreasing cells 10-20% spreading effect 30-40% max morphology 50-60% gives more 3D-growth |
| Number of cells | No effect | Increasing | Max 20-30% 40-60% decreasing | Decreasing | Max 20-30% 40-60% decreasing | Increasing |

Example 4

Effect of Sterilisation of ECM+/−Incorporation in Scaffolds on the Cell Morphology and 3D Growth of Primary Fibroblasts Metoxy-polyethylene glycol—Poly(lactide-co-glycolide) (Mn 2.000-30.000, L:G 1:1) was dissolved in 1,4-dioxane to a 1.5% solution. For UBM containing samples, 0.045 g non-sterilized UBM was added to 10 ml polymer solution (23% w/w drymatter), high-speed-mixed and poured in 7×7 cm mould. The solution was frozen at −5° C. and lyophilized at −20° C. for 5 h and 20° C. for approx 18 h. The samples were subsequently placed in draw (hydraulic pump) in a desiccator for 15 h.

The samples with and without UBM were beta radiated by 0, 1×25 kGy and 2×25 kGy. Another sample was prepared in the same way, but a pre-sterilized UBM (2×25 kGy beta radiation) was used (0.045 g/5 ml solution) and the sample was not sterilized after preparation.

Gelatin from porcine skin, type A, bloom 175 (Sigma) was dissolved in milli-Q water and t-BuOH (95:5) to a 1% solution. 0.015 g non-sterilized UBM was added to 5 ml solution (23% w/w drymatter) while stirring and poured into the mould (D=5 cm). The mould with the solution was placed in +5° C. for 2 h, then frozen at −20° C. and lyophilized at −20° C. for 5 h and at 20° C. for 20 h. The samples were subsequently cross-linked in vacuum oven at 120° C. for 15 h. The samples with and without UBM were beta radiated by 0 and 1×25 kGy and 2×25 kGy. Another sample was prepared in the same way without UBM. The samples were sterilized after preparation at 0, 1×25 kGy and 2×25 kGy.

Gelatin from porcine skin, type A, bloom 175 (Sigma) was dissolved in milli-Q water and t-BuOH (95:5) to a 1% solution. 0.015 g pre-sterilized UBM (1×25 kGy) was added to 5 ml solution (23% w/w drymatter) while stirring and poured into the mould (D=5 cm). The mould with the solution was placed in +5° C. for 1 h, then frozen at −20° C. and lyophilized at −20° C. for 5 h and at 20° C. for 50 h. The samples were subsequently cross-linked in vacuum oven at 130° C. for 15 h.

The cell morphology and 3D growth study showed that an increasing radiation of UBM sheets reduced the number of cells on the UBM sheets but with no effect on the morphology of the cells. In the gelatine scaffold and gelatine with 30% (w/w) UBM a decreasing number of cells and a change in morphology from typical fibroblastic cells to a more rounded one was seen with the largest effect seen in the gelatine scaffold. Sterilisation of UBM particles before incorporation in gelatine scaffolds gives a better cell morphology and 3D growth compared to incorporation of UBM particles before sterilisation of the scaffold. In the MPEG-PLGA an increasing radiation resulted in an increased number of cells with fibroblastic morphology due to increased moistening of the scaffold. Radiation of scaffolds of MPEG-PLGA containing 30% (w/w) UBM resulted in an even higher number of cells and a more 3D morphology of the fibroblasts also compared with scaffold where the UBM particles were radiated before incorporation into the scaffold.

This study showed that the highest biological activity was achieved in the non-radiated gelatine scaffold and that radiation decreased the activity. On the contrary the highest biological activity was found when the UBM particles were incorporated in the MPEG-PLGA scaffold, and subsequently sterilized. It is believed that radiation decreases the biological activity of UBM. Radiation can affect the scaffold material in a negative or positive way depending on the material in relation to biological activity. There are indications showing that the scaffold material (e.g. MPEG-PLGA) can have a protective effect of the UBM during sterilization.

Example 5

Discrete Particles of ECM in MPEG-PLGA

Scaffolds of MPEG-PLGA containing 41% (w/w) of UBM particles were seeded with primary fibroblasts on the surface of the scaffolds with a density of $2.5 \times 10^4$ cells/cm$^2$ in a small volume of growth medium (10% FCS in DMEM containing antibiotics (penicillin, streptomycin and Amphotericin B). The scaffolds were incubated at 37° C. at 5% $CO_2$ before additional growth medium was added. After 7 days the scaffolds were placed in Lillys fixative for 3 days before embedding in paraffin, sectioning into 8 μm slices and staining by Meyer's haematoxylin erosion (HE). Digital images (4× and 20× magnifications) were collected using a BX-60 Olympus microscope fitted with an Evolution MP cooled colour camera (Media Cybernetics) and digital image were taken using Image Pro Plus 5.1 software.

Digital images of the distribution of ECM particles in the MPEG-PLGA scaffold showed discrete UBM particles stained red by HE and distinguish from the scaffold material. Fibroblasts growing in the scaffold were stained blue (FIG. 7).

Example 6

Discrete Particles of UBM in MPEG-PLGA Shown by SEM

Scaffolds were prepared as described in Example 1.

The SEM pictures are showing MPEG-PLGA scaffolds with (FIG. 9) and without (FIG. 8) UBM particles. The pictures are taken at the top surface of the scaffold at a magnitude of 250. The SEM pictures were taken at the Danish technological institute (2005-160).

Example 7

Three Dimensional Endothelial Growth and Differentiation in Scaffolds Holding ECM Particles Metoxy-polyethylene glycol—Poly(lactide-co-glycolide) (Mn 2.000-30.000, L:G 1:1) was dissolved in 1,4-dioxane to a 1.5% solution. For UBM containing samples, 0.045 g non-sterilized UBM was added to 10 ml polymer solution (23% w/w drymatter), high-speed-mixed and poured in 7×7 cm mould. The solution was frozen at −5° C. and lyophilized at −20° C. for 5 h and 20° C. for approx 16 h. The samples were subsequently placed in draw (hydraulic pump) in a desiccator for 15 h.

Primary human endothelial cells from umbilical cord were co-cultured with primary human dermal fibroblasts on the surface of MPEG-PLGA scaffolds and scaffold containing 23% (w/w) UBM. The constructs were cultured submerged in defined endothelial growth medium for 6-10 days after which they are airlifted and cultured for another 9 days. On the final day of culture constructs were fixed with 4% formalin buffer, bisected and paraffin embedded.

By immunohistochemical peroxidase staining of CD31/PECAM (platelet endothelial cell adhesion molecule) endothelial cells were visualized on 5 μm sections. Identifying fibroblasts, parallel sections were stained with PECAM peroxidase combined with a haematoxylin counterstain. As endothelial growth and differentiation is influenced by fibroblast performance, all scaffold materials were tested with 2 different fibroblast populations but were not giving rise to different results.

All MPEG-PLGA scaffolds support fibroblast and endothelial growth. Fibroblasts were found throughout the entire volume of all MPEG-PLGA scaffolds. UBM particles were homogenously distributed and scaffolds remain intact during culture. Culturing endothelial cells and fibroblasts on MPEG-PLGA scaffolds however brings endothelial surface growth only—endothelial cells proliferate within a matrix produced by the neighboring fibroblasts on top of the scaffold. Adding UBM particles promote fibroblast and endothelial growth in the deeper layers of the scaffolds and endothelial cells adopt capillary-like morphology. Endothelial cells are guided along the surface of UBM particles rather than migrating into them. Therefore we find that including UBM particles in scaffolds lead to a very distinct improvement in endothelial growth and differentiation. The different fibroblast populations were not giving rise to different results.

MPEG-PLGA scaffolds (FIG. 10) and 23% (w/w) UBM in MPEG-PLGA (FIG. 11) show growth of endothelial cells in the surface of the MPEG-PLGA scaffold where the growth is into the depth holding UBM particles (endothelium is stained red (shown black)—fibroblasts are not visible).

Capillary-like morphology of endothelial cells were seen in the deeper layer of MPEG-PLGA scaffold holding 23% (w/w) UBM (FIG. 12). These structures were not seen in the MPEG-PLGA scaffold.

Example 8

Physical and Mechanical Properties of Scaffolds Containing Different Concentrations of ECM Particles Samples prepared:
Freeze-dried scaffold with gelatin matrix
Freeze-dried scaffold with gelatin matrix and 40 w/w UBM particles
Freeze-dried scaffold with gelatin matrix and 80 w/w UBM particles.

Gelatin from porcine skin, type A (PG-832-6 Gelita) was dissolved in milli-Q water and t-BuOH (95:5) to a 1% solution. For UBM containing samples, UBM was added to the solution while stirring (40% w/w: 0.033 g/5 ml, 80% w/w: 0.2 g/5 ml). 5 ml of the UBM containing gelatin solution was poured into the mould (D=5 cm). The mould with the solution was placed in +5° C. for 2.5 h, then frozen at −20° C. and lyophilized at −20° C. for 5 h and at 20° C. for 100 h. The samples were subsequently cross-linked in vacuum oven at 130° C. for 15 h.

Samples prepared:
Freeze-dried scaffold with PLGA matrix
Freeze-dried scaffold with PLGA matrix and 40% (w/w) UBM particles
Freeze-dried scaffold with PLGA matrix and 80% (w/w) UBM particles.

Metoxy-polyethylene glycol—Poly(lactide-co-glycolide) (Mn 2.000-30.000, L:G 1:1) was dissolved in 1, 4-dioxane to a 1.5% solution. For UBM containing samples, UBM was added to the polymer solution (40% (w/w): 0.1 g/10 ml, 80% (w/w): 0.6 g/10 ml), high-speed-mixed and poured in 7×7 cm mould. The solution was frozen on a 1,4-dioxane layer at −5° C. and lyophilized at −20° C. for 5 h and 20° C. for approx 100 h. The samples were subsequently placed in draw (hydraulic pump) in a desiccator for 15 h.

Physical Properties and Mechanical Testing

Depending on the matrix material and the amount of UBM added, different physical and mechanical properties can be achieved.

The porosity decreases with the amount of UBM added, thus the density increases.

If the matrix is hydrophobic, the UBM will provide increased wet ability.

Gelatin scaffolds retain its tensile strength up to at least 40% (w/w) UBM, after which it decreases, whereas PLGA scaffolds are slightly strengthened by the UBM particles. The low material concentration in combination with the freeze-drying process gives low tensile strength, which is also the case for the samples in this example.

| Gelatin | Height (mm) | Density (mg/cm3) | Porosity (%) | Wet ability (min) |
|---|---|---|---|---|
| 0% UBM | 1.6 (±0.1) | 15 (±1) | 99 (±0) | instant |
| 40% UBM | 1.6 (±0.0) | 24 (±1) | 97 (±0) | instant |
| 80% UBM | 1.6 (±0.0) | 73 (±0) | 72 (±0) | instant |

| PLGA | Height (mm) | Density (mg/cm3) | Porosity (%) | Wet ability (min) |
|---|---|---|---|---|
| 0% UBM | 1.2 (±0.0) | 26 (±3) | 98 (±0) | >45 |
| 40% UBM | 1.3 (±0.0) | 36 (±2) | 96 (±0) | 5 < x < 15 |
| 80% UBM | 1.6 (±0.0) | 94 (±8) | 65 (±3) | <2 |

Height is measured with a slide gauge.
Density is calculated as:

$$\text{Density} = \text{Mass}/(\text{Area} \times \text{Height})$$

Porosity is calculated as:

$$\text{Porosity} = (\text{polymer density} - \text{sample density})/\text{polymer density}.$$

The polymer density is weight adjusted according to added UBM (3 mg/cm$^3$).

Wet ability is calculated as the amount of time for a droplet of water to be fully absorbed by the sample, photo monitored.

| Gelatin | Tensile Force max (N) |
|---|---|
| 0% UBM | 0.20 (±0.07) |
| 40% UBM | 0.20 (±0.02) |
| 80% UBM | 0.02 (±0.00) |

| PLGA | Tensile Force max (N) |
|---|---|
| 0% UBM | 0.01 (±0.00) |
| 40% UBM | 0.02 (±0.00) |
| 80% UBM | 0.04 (±0.01) |

Tensile testing was carried out on a Texture Analyzer from Stable Micro Systems.

The invention claimed is:

1. A composite scaffold comprising discrete cell free ECM material in a micronized form incorporated into a temporary scaffold.

2. The composite scaffold according to claim 1, wherein the concentration of ECM is between 20% (w/w) and 60% (w/w).

3. The composite scaffold according to claim 2, wherein the temporary scaffold is biodegradable.

4. The composite scaffold according to claim 3, wherein the biodegradable temporary scaffold includes one or more protein containing substances.

5. The composite scaffold according to claim 3, wherein the biodegradable temporary scaffold includes one or more polysaccharide containing substances.

6. The composite scaffold according to claim 3, wherein the biodegradable temporary scaffold includes one or more synthetic polymer containing substances.

7. The composite scaffold according to claim 3, wherein the biodegradable temporary scaffold includes a material selected from the group consisting of protein containing substances, polysaccharide containing substances, synthetic polymer containing substances, and any combination thereof.

8. The composite scaffold according to claim 2, wherein the ECM material is homogeneously distributed.

9. The composite according to claim 2, wherein the temporary scaffold has open interconnected pores.

10. The composite material according to claim 2, wherein the scaffold has a thickness of 0.1-8 mm.

11. The composite scaffold according to claim 2, wherein the composite scaffold is packaged bacterial tight, with a marking on the package that this product is sterilized.

* * * * *